United States Patent
Gayzik et al.

(10) Patent No.: US 10,736,691 B2
(45) Date of Patent: Aug. 11, 2020

(54) SURFACE ENERGY ENHANCEMENT OF LUBRICIOUS OBJECTS

(71) Applicant: Cook Medical Technologies LLC, Bloomington, IN (US)

(72) Inventors: Caroline Gayzik, Winston-Salem, NC (US); Stephanie Rivera, Burlington, NC (US); Shaq Abdelhaq, Greensboro, NC (US); Roger Neil Saunders, Yadkinville, NC (US)

(73) Assignee: Cook Medical Technologies LLC, Bloomington, IN (US)

( * ) Notice: Subject to any disclaimer, the term of this patent is extended or adjusted under 35 U.S.C. 154(b) by 260 days.

(21) Appl. No.: 14/751,994

(22) Filed: Jun. 26, 2015

(65) Prior Publication Data

US 2015/0374434 A1 Dec. 31, 2015

Related U.S. Application Data

(60) Provisional application No. 62/017,638, filed on Jun. 26, 2014.

(51) Int. Cl.
*A61B 18/14* (2006.01)
*A61M 25/00* (2006.01)
(Continued)

(52) U.S. Cl.
CPC ..... *A61B 18/1492* (2013.01); *A61M 25/0009* (2013.01); *B29C 63/42* (2013.01);
(Continued)

(58) Field of Classification Search
CPC ........... A61B 2018/00136; A61B 2018/00226; A61B 2018/005; A61B 2018/00553;
(Continued)

(56) References Cited

U.S. PATENT DOCUMENTS

| 4,522,212 A * | 6/1985 | Gelinas | A61N 1/368 600/374 |
| 5,035,696 A * | 7/1991 | Rydell | A61B 18/14 606/47 |
| 5,156,151 A * | 10/1992 | Imran | A61N 1/056 600/375 |
| 5,308,324 A | 5/1994 | Hammerslag et al. | |

(Continued)

FOREIGN PATENT DOCUMENTS

CA 2 164 022 5/1996
WO WO 99/38557 8/1999

OTHER PUBLICATIONS

"Evaluation of wettability and surface energy of native Nitinol surfaces in relation to hemocompatibility". Shabalovskaya et al. Materials Science & Engineering. C, Materials for Biological Applications. Jan. 1, 2013;33(1):127-32. doi: 10.1016/j.msec.2012.08.018. Epub Aug. 20, 2012. <https://www.ncbi.nlm.nih.gov/pubmed/25428053> (Abstract).*

*Primary Examiner* — Jaymi E Della
*Assistant Examiner* — Sean W Collins
(74) *Attorney, Agent, or Firm* — Brinks Gilson & Lione (57) ABSTRACT

A surface of an object comprises a material having a low surface energy. A first cover comprising a material having a higher surface energy than the surface of the object may cover and be affixed to the surface. A second cover may be adhered to and/or secured by the first cover so that the second cover is fixedly coupled to the surface of the object.

10 Claims, 8 Drawing Sheets

(51) Int. Cl.
*B29C 63/42* (2006.01)
*A61B 18/00* (2006.01)
*A61B 18/16* (2006.01)
*A61B 90/00* (2016.01)

(52) U.S. Cl.
CPC ............... *A61B 2018/005* (2013.01); *A61B 2018/00077* (2013.01); *A61B 2018/00136* (2013.01); *A61B 2018/00226* (2013.01); *A61B 2018/00601* (2013.01); *A61B 2018/162* (2013.01); *A61B 2090/3966* (2016.02)

(58) Field of Classification Search
CPC ...... A61B 2018/162; A61B 2090/3966; A61B 2018/1407; A61B 2018/144; A61B 18/1492; A61B 2262/164; A61B 2262/166; A61B 2262/22; A61B 5/0215; A61B 5/04; A61B 5/04001; A61B 5/0402; A61B 5/0476; A61B 5/6852–6859; B29C 63/42; A61N 1/0472; A61N 1/05–0563; A61N 1/06; A61M 25/0009; A61M 25/0012
See application file for complete search history.

(56) References Cited

U.S. PATENT DOCUMENTS

| | | | |
|---|---|---|---|
| 5,462,545 A * | 10/1995 | Wang | A61B 18/1492 600/373 |
| 5,807,309 A * | 9/1998 | Lundquist | A61M 25/0136 604/22 |
| 5,827,201 A | 10/1998 | Samson et al. | |
| 6,197,014 B1 | 3/2001 | Samson et al. | |
| 7,597,830 B2 | 10/2009 | Zhou | |
| 8,637,132 B2 | 1/2014 | Bavaro et al. | |
| 8,668,657 B2 | 3/2014 | Solar et al. | |
| 2001/0026666 A1 | 10/2001 | Ferrera et al. | |
| 2003/0135198 A1 | 7/2003 | Berhow et al. | |
| 2006/0047224 A1 | 3/2006 | Grandfield | |
| 2007/0106292 A1 * | 5/2007 | Kaplan | A61B 18/1492 606/41 |
| 2007/0282358 A1 * | 12/2007 | Remiszewski | A61B 17/00 606/159 |
| 2008/0188832 A1 | 8/2008 | Tanioka et al. | |
| 2009/0318746 A1 * | 12/2009 | Thurmond, II | A61L 29/041 600/8 |
| 2010/0004632 A1 | 1/2010 | Wu et al. | |
| 2011/0319758 A1 * | 12/2011 | Wang | A61B 17/3403 600/439 |
| 2012/0010490 A1 * | 1/2012 | Kauphusman | A61B 5/0422 600/373 |
| 2014/0081292 A1 | 3/2014 | Moll et al. | |

* cited by examiner

SURFACE ENERGY ENHANCEMENT OF LUBRICIOUS OBJECTS

CROSS-REFERENCE TO RELATED APPLICATIONS

This application claims the benefit of U.S. Provisional Application No. 62/017,638, filed on Jun. 26, 2014. The contents of U.S. Provisional Application No. 62/017,638 are incorporated by reference in their entirety.

TECHNICAL FIELD

The present invention relates generally to medical devices and more particularly to application of a first cover to a surface to enhance the coupling of a second cover to the surface.

BACKGROUND

A medical device may include a catheter made of a low surface energy material that, while having high lubricious and insulating characteristics, provides a surface that is difficult for the other materials to adhere to it. To increase the strength of the adhesion of the surface, a secondary surface preparation process, such as blasting, etching, or plasma treatment, may be performed. However, these processes may be timely or costly, and/or may undesirably discolor or tint the catheter, which in turn may diminish or eliminate visual access to within the catheter.

BRIEF SUMMARY

In a first aspect, an elongate member may include a body that has an outer surface, where the outer surface comprises a first material having a first surface energy. The elongate member may further include a first cover disposed on the outer surface of the body, where the first cover comprises a second material having a second surface energy that is greater than the first surface energy. The elongate member may further include a second cover disposed on the first cover. The first cover may fixedly couple the second cover to the outer surface of the body.

In a second aspect, an elongate member may include a body comprising an outer surface; one or more bands disposed about the outer surface of the body; and a heat shrink tube disposed over the outer surface and covering the one or more bands.

In a third aspect, a method of coupling a second cover to a surface of an object may include affixing a first cover to the surface of the object, where the surface of the object comprises a first material having a first surface energy, and where the first cover comprises a second material having a second surface energy that is greater than the first surface energy. The method may further include; affixing the second cover to the first cover, where the second cover is fixedly coupled to the surface of the object upon being affixed to the first cover.

In a fourth aspect, a method of securing one or more bands to an elongate member may include: disposing the one or more bands about the elongate member; disposing a heat shrink tube over the one or more bands; and applying heat to the heat shrink tube.

DETAILED DESCRIPTION

The present description describes application of a first cover to a surface of an object to fixedly couple a second cover to the surface. Without the first cover, the second cover may be unable to be sufficiently coupled to the surface of the object. For example, the object, or at least the surface of the object, may be made of a material having a relatively low surface energy. Surface energy, which may be quantified as energy per square area (e.g., $mJ/m^2$), may be a measurement of and/or indicate a strength of adhesion of the material. As a general rule, the higher the surface energy, the greater the strength of adhesion. Accordingly, those surfaces made of a material having a relatively low surface energy may be less suitable for materials to adhere to it compared to surfaces made of a material having a relatively high surface energy. For purposes of the present description, low surface energy may be less than or equal to 37 $mJ/m^2$, and high surface energy may be greater than 37 $mJ/m^2$.

A contact angle, which may quantify the wettability of a material, may be indicative of the surface energy of the material. As a general rule, the lower the contact angle, the higher the surface energy. Accordingly, those surfaces with higher contact angles may have a lower strength of adhesion than surfaces with lower contact angles. For purposes of the present description, materials with contact angles greater than 72 degrees may be low surface energy materials, while materials with contact angles less than 72 degrees may be high surface energy materials.

For polymeric materials, a non-exhaustive list of high surface energy polymers may include: polyimide (e.g., Kapton® polyimide film), phenolic, nylon, alkyd enamel, polyester, epoxy paint, polyurethane paint, acrylonitrile butadiene styrene (ABS), polycarbonate, rigid polyvinyl chloride (PVC), polyphenylene ether (PPE) (e.g., Noryl™ resin), and acrylic. A non-exhaustive list of low surface energy polymers may include: polyvinyl alcohol (PVA), polystyrene, acetal, ethylene vinyl acetate (EVA), polyethylene, polypropylene, polyvinyl fluoride (PVF) (e.g., Tedlar® polyvinyl fluoride film), and polytetrafluoroethylene (PTFE) (e.g., Teflon® fluoropolymer).

Objects, or at least their surfaces, may be made of a low surface energy material for various reasons. For example, in the field of medical devices, elongate members, such as catheters, endoscopes, wire guides, stylets, or the like, may be made of and/or coated with a low surface energy material. Such low surface energy material may be desirable due to the material's lubricious and/or insulating properties. However, the low-degree of adhesive strength of the material may provide an inadequate surface for adhering certain materials, such as ink, paste, or adhesives. To increase the adhesive strength of the surface, a secondary surface preparation process, such as blasting, etching, or plasma treatment, may be performed on the elongate member. However, such secondary processes may be timely and/or costly. Additionally, one or more of the secondary processes may undesirably discolor, such as darken or diminish the transparency of, the elongate member. Such darkening may be undesirable because it diminishes or eliminates visible access to within the elongate member, such as to monitor wire guides or other devices being moved within one or more lumens of the elongate member.

The present description describes application of a first cover to a surface of an object to increase a surface energy of an area over which the first cover covers the surface. In turn, the area being covered by the first cover may have a greater strength of adhesion for adhering a second cover covering the surface to the object. To increase the surface energy of the area, the first cover has a surface energy that is greater than the surface energy of the surface of the object. For some example configurations, the surface of the object has a low surface energy, whereas the first cover has a high surface area, although for other example configurations, the surface of the object and the first cover are both made of low surface energy materials, or both made of high face energy materials.

FIGS. 1-6 show various example embodiments of elongate members used in the medical device field, each having a body with an outer surface, a first cover, and a second cover, where each cover covers and/or is disposed over an area of the outer surface. For at least some of the embodiments, the first cover may comprise a material that has a greater surface energy than a surface energy of the outer face of the body. Through application of the first cover to the outer surface of the body, a second cover may be more fixedly coupled or securely attached to the body over at least a portion of the area, than if the first cover was not included.

For the example elongate members shown in FIGS. 1-6 the first cover is described as being configured as a heat shrink tube having an original diameter that decreases (or shrinks) in response to heat. When the original diameter deceases, an inwardly radial force may be exerted on the outer surface by the heat shrink tube, which affixes the heat shrink tube to the elongate member.

Figure 1:
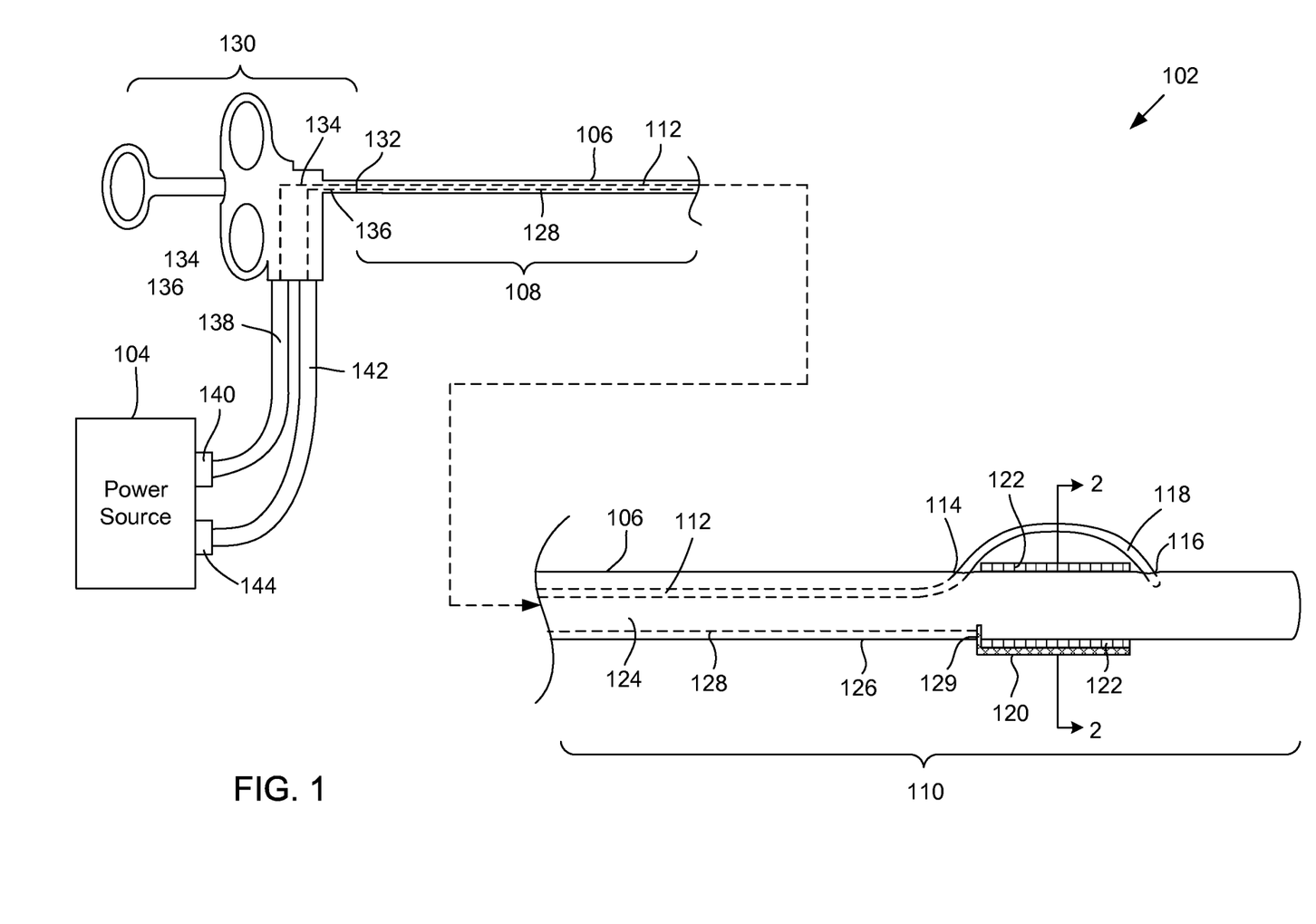
FIG. 1 is a cross-sectional side view of an example bipolar sphincterotome that includes a distal portion of an elongate member.

FIG. 1 shows a cross-sectional side view of an example bipolar sphincterotome 102 configured to perform a sphincterotomy. As shown in FIG. 1, the bipolar sphincterotome 102 may be electrically connected to a power source 104. The power source 104 may be an electronic device, such as a radio frequency (RF) generator or an electrosurgical unit (ESU) that is configured to generate and supply electrical current to the bipolar sphincterotome 102 for performance of the sphincterotomy. The bipolar sphincterotome 102 may include an elongate tubular member 106 that longitudinally extends from a proximal portion 108 to a distal portion 110. The bipolar sphincterotome 102 may also include an active path and a return path that may be electrically coupled to the power source 104. The active path may be configured to deliver electrical current from the power source 104 to a treatment site, and the return path may return the electrical current back to the power source 104.

The active path may include an elongate conductive member 112, such as a cutting wire or a flat metal strip, that is used to cut the sphincter muscle. The conductive member 112 may longitudinally extend within a cutting wire lumen (not shown in FIG. 1) from the proximal portion 108 to the distal portion 110. At the distal portion 110, the conductive member 112 may extend or protrude from within the tubular member 106, through a first opening 114 of the tubular member 106, to outside the tubular member 106. Outside the tubular member 106, an exposed portion 118 of the conductive member 112 may longitudinally extend substantially parallel with the tubular member 106 to a second opening or anchor point 116 of the tubular member 106 that is distal to the first opening 114, where a distal end of the conductive member 112 may re-enter and/or be fixedly attached to the tubular member 106. The exposed portion 118 of the conductive member 112 may be referred to as a cutting edge, which may be the portion of the conductive member 112 that cuts tissue (e.g., the sphincter muscle) at the treatment site.

In accordance with a bipolar configuration, the return path of the bipolar sphincterotome 102 may be attached to, adhered to, integrated with, disposed within, or included as part of the tubular member 106. The bipolar configuration may differ from a monopolar configuration, which may use a neutral electrode (e.g., a solid, neutral electrode or a split neutral electrode) positioned on a thigh of the patient as part of the return path.

The return path may include a return electrode 120 disposed at the distal portion 110 of the tubular member 106. The return electrode 120 may be a portion of the return path that is configured to contact tissue at the treatment site. Accordingly, the return electrode 120 may be a conductive, exposed portion of the return path that is exposed to the outer surroundings of the bipolar sphincterotome 102 at the distal portion 110 so that the return electrode 120 may contact the tissue. Various configurations and/or orientations of the return electrode 120 are possible, examples of which are The return electrode 120 may be disposed over and/or cover an outer surface 126 of a body 124 of the tubular member 106. The body 124, or at least the outer surface 126 of the body 124, may be made of a material that has low surface energy. An example material may be PTFE, although other low surface energy materials as previously described are possible. The return electrode 120 may be made of a relatively thin conductive material such as ink, paste, paint, tape, adhesive, or combinations thereof as examples. Due to the low surface energy of the outer surface 126, the adhesive strength of the outer surface 126 may be inadequate for directly adhering the return electrode 120 to the outer surface 126.

Various configurations and/or orientations about the outer surface 126 of the return electrode 120 are possible, examples for which are shown and described in U.S. application Ser. No. 14/139,214, filed Dec. 23, 2013, the contents of which are incorporated by reference in their entirety.

As shown in FIG. 1, a heat shrink tube 122 may be disposed over and cover the outer surface 126 at the distal portion 110. By being heat shrunk, the heat shrink tube 122 may be affixed to and/or fixedly coupled to the outer surface 126 of the body 124. In addition, the heat shrink tube 122 may be made of a high surface energy material. Because the heat shrink tube 128 is made of a high surface energy material, it may provide a surface with strong enough adhesion for the return electrode to be fixedly coupled to it. As such by being adapted to be affixed to each the outer surface 126 of the body 124 and the return electrode 120, the heat shrink 128 may fixedly couple the return electrode 120 to the body 124.

Example high surface energy materials for the heat shrink tube 122 may be nylon or polyurethane, although other high surface energy materials are possible, as previously described. Additionally, various parameters or specifications for the heat shrink tube 122 may be possible. An example material for the heat shrink tube 122 may be Pebax®, although other materials may be used. In addition or alternatively, a thickness of the heat shrink tube 122 may be in a range of about 0.002 to 0.020 inches, although other thicknesses may be possible. In addition or alternatively, a durometer of the heat shrink tube 122 may be less than or equal to Shore 40A. In addition or alternatively, the heat shrink tube 122 may be clear, tinted, solid colored, pre-printed with information/patterns, or have unique surface textures.

Figure 1A:
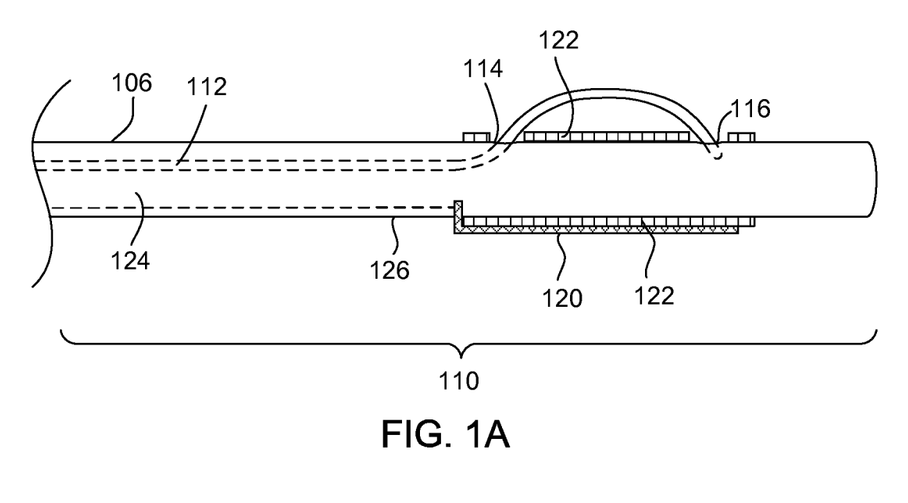
FIG. 1A is a cross-sectional side view of a first alternative configuration of the distal portion of the bipolar sphincterotome of FIG. 1.
Figure 1B:
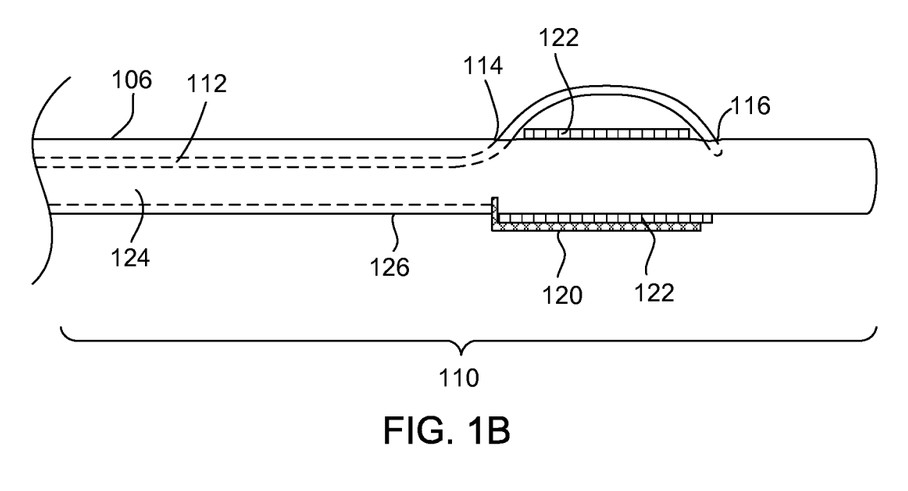
FIG. 1B is a cross-sectional side view of a second alternative configuration of the distal portion of the bipolar sphincterotome of FIG. 1.

Additionally, the heat shrink tube 122 may have any longitudinal positioning at the distal portion 110 relative to the first opening 114 and/or the second opening 116. For the example embodiment shown in FIG. 1, the heat shrink tube 122 may longitudinally extend entirely in between the first opening 114 and the second opening 116. In alternative embodiments, the heat shrink tube 122 may longitudinally extend proximally past the first opening 114 and/or distally past the second opening 116, as shown in FIG. 1A; may be substantially even with the first opening 114 and/or the second opening 116 as shown in FIG. 1B, or combinations thereof. For still other alternative embodiments, the heat shrink tube 122 may proximally extend all the way to the proximal portion 108 of the elongate member 106, may be longitudinally disposed completely proximal the first opening 114, completely distal the second opening 116, or combinations thereof. Some or all of the alternative embodiments, including those shown in FIGS. 1A and 1B, may allow for a larger return electrode to be coupled to the body 124. Also, for any of the example embodiments, the heat shrink tube 122 may include a single tube or a plurality of tubes. Various configurations of the number of tubes used and/or longitudinal positioning of the one or more heat shrink tubes are possible.

Referring back to FIG. 1, the return path may also include a conductive, unexposed member 128 electrically connected to the return electrode 120. The unexposed member 128 may be disposed distal the return electrode 120 and configured to deliver electrical current from the return electrode 120 back to the power source 104. The unexposed member 128 may be unexposed to the outer surroundings of the bipolar sphincterotome 102 and/or be the portion of the return path that is configured to not contact tissue within the patient. In the example configuration shown in FIG. 1, the unexposed member 128 may longitudinally extend within the body 124 of the tubular member 106 from the proximal portion 108 to the distal portion 110, where the unexposed member 128 is electrically connected to the exposed, return electrode 120. In alternative example configurations, all or some of the unexposed member 128 may longitudinally extend outside of body 124, such as alongside the outer surface 126. For these configurations, the unexposed member 128 may be encased or coated with an insulating material so that the conductive material of the unexposed member 128 does not contact the tissue.

As shown in FIG. 1, a coupler 129 may electrically couple the return electrode 120 with the unexposed member 128 of the return path. The coupler 129 may be implemented in any number of different ways and is considered outside the scope of the present description.

The bipolar sphincterotome 102 may further include a handle assembly 130 coupled to a proximal end 132 of the tubular member 106. The handle assembly 130 may be operatively coupled to a proximal end 134 of the active conductive member 112, and configured to proximally and distally move the active conductive member 112 to position the distal portion 110 of the tubular member in taut and relaxed positions during use of the bipolar sphincterotome 102. In addition, as shown in FIG. 1, the proximal end 134 of the active conductive member 112 and a proximal end 136 of the unexposed member 128 may each be electrically coupled to the power source 104 via the handle assembly 130, although alternative configurations may be possible. An active power cord 138 may be connected to an active port 140 of the power source 104 and to the handle assembly 130 to electrically couple the active port 130 of the power source 104 with the active conductive member 112. Similarly, a return power cord 142 may be connected to a return port 144 of the power source 104 and to the handle assembly 130 to electrically couple the unexposed member 128 of the return path to the return portion 144 of the power source 104.

Figures 2A, 2B, 2C:
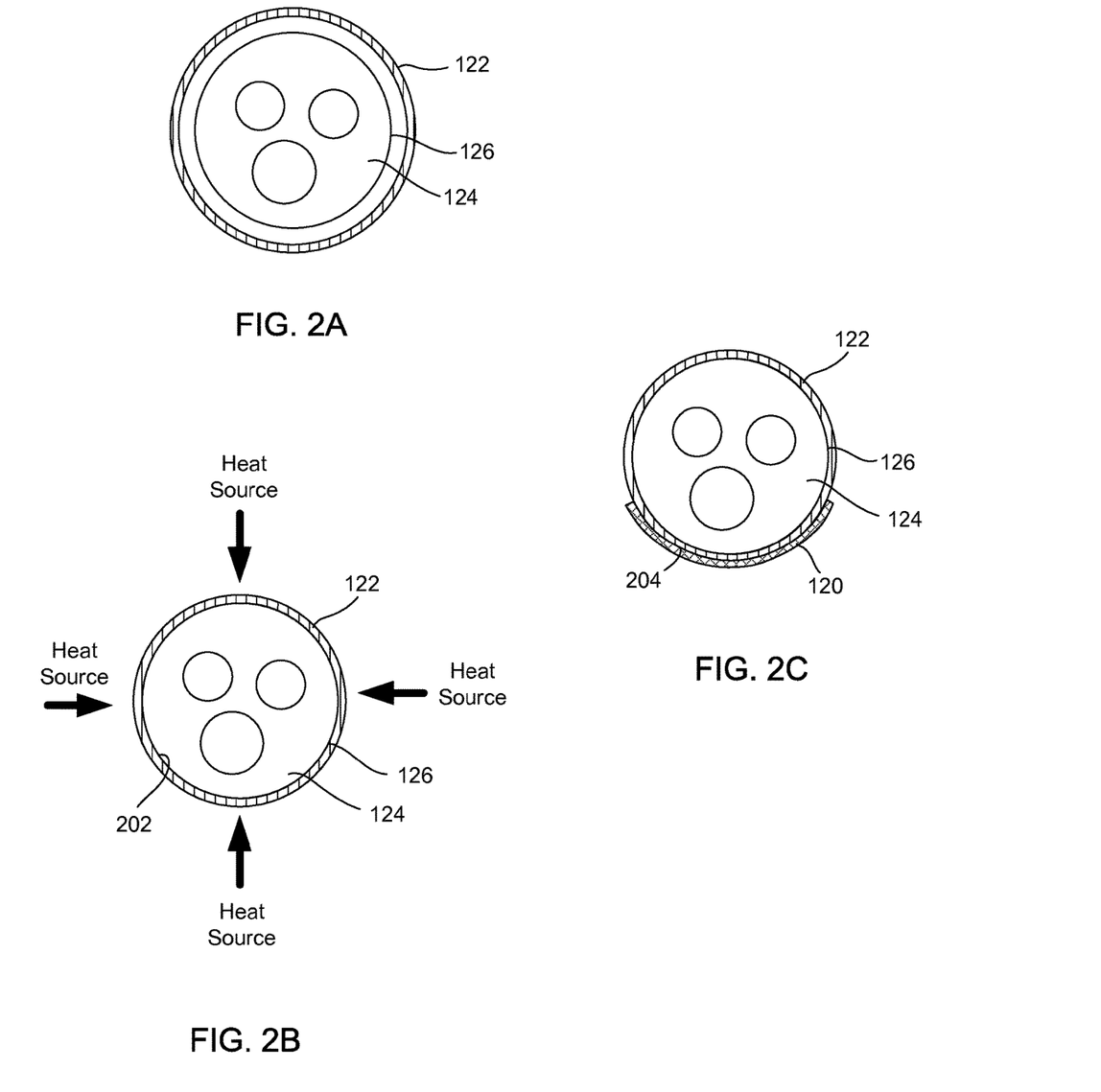
FIG. 2A is a cross-sectional axial view of the bipolar sphincterotome of FIG. 1 taken along lines 2-2, where the heat shrink tube is in an initial state and the return electrode is not yet affixed to the heat shrink tube.
FIG. 2B is a cross-sectional axial view of the bipolar sphincterotome of FIG. 1 taken along lines 2-2, where the heat shrink tube is in a shrunken state and the return electrode is not yet affixed to the heat shrink tube.
FIG. 2C is a cross-sectional axial view of the bipolar sphincterotome of FIG. 1 taken along lines 2-2, where the heat shrink tube is in the shrunken state and the return electrode is affixed to the heat shrink tube.

A method of affixing the return electrode 120 to the outer surface 126 of the body 120 is made with reference to FIGS. 2A-2C, which are cross-sectional axial views of the bipolar sphincterotome 102 taken along line 2-2 in FIG. 1. As shown in FIG. 2A, the heat shrink tube 122 in an unheated state, may be circumferentially disposed about the outer surface 126 of the body 124. In the unheated state, an original inner diameter of the heat shrink tube 122 may be about the same size or greater than an outer diameter of the body 124. As shown in FIG. 2B, the heat shrink tube 122 may be subjected to heat from a heat source, which may cause the inner diameter of the heat shrink tube 122 to shrink. Various heat sources may be used to heat the heat shrink tube, including a glow ring, an oven, hot air, or a heat gun as non-limiting examples. In heating the heat shrink tube 122, an inner surface 202 of the heat shrink tube may contact and exert a force on the outer surface 126 of the body 124, which may affix the heat shrink tube 122 to the outer surface 126. In addition or alternatively to heating the heat shrink tube 122, other actions may be taken on the heat shrink tube 122 to further affix and/or enhance attachment of the heat shrink tube 122 to the outer surface 126, including crimping or swaging or applying adhesives, as examples.

In addition to affixing the heat shrink tube 122 to the outer surface 126, the return electrode 120 may be affixed to an outer surface 204 of the heat shrink tube 122. Any number of actions may be taken to affix the return electrode 120 to the heat shrink tube 122, including manual application, pad print, or spraying as non-limiting examples.

Although FIGS. 1, 1A, 1B, 2A-2C show a heat shrink tube 122 used to fixedly couple the return electrode 120 to the outer surface 126 for a bipolar sphincterotome, similar configurations may be implemented for any other type bipolar or monopolar electrosurgical device that may utilize an electrically conductive material or electrode disposed over or covering a portion of an outer surface of a body an elongate tubular member, including needle knives, snares, or forceps as non-limiting examples.

Figure 3:
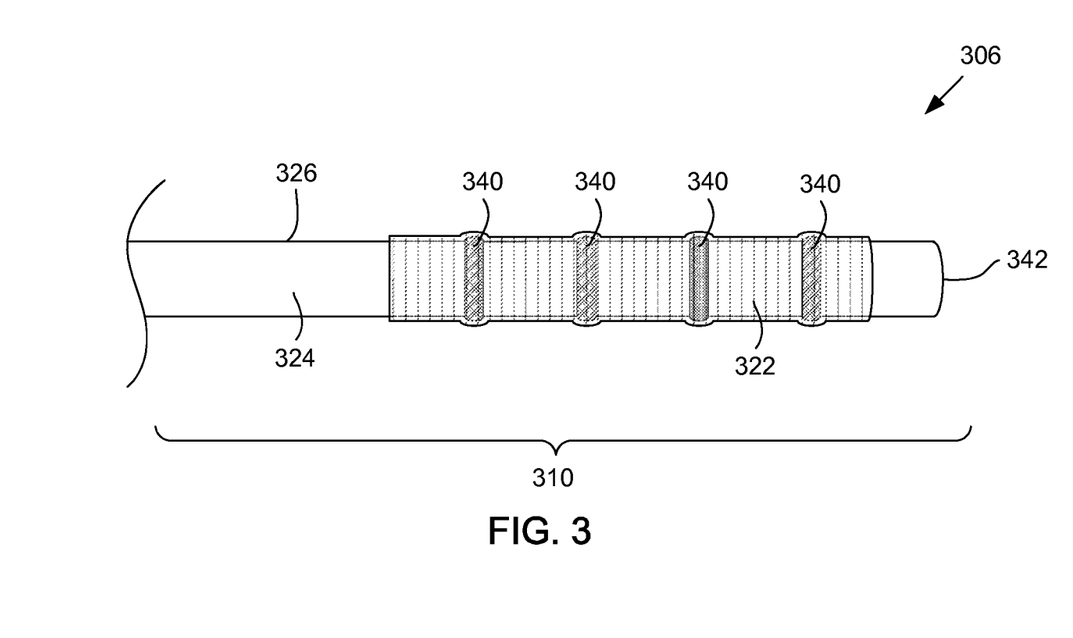
FIG. 3 shows a perspective side view of a distal portion of an elongate member with bands disposed about an outer surface and a heat shrink tube disposed over the bands.

FIG. 3 shows a perspective side view of an example embodiment of a distal portion 310 of an elongate member 306 that includes one or more bands 340 or other similar tubular structures disposed over an outer surface 326 of a body 324 of the elongate member 306. The material for the body 324 may be any material, including a high surface energy or a low surface energy material. For some applications of elongate members with bands, including those in the field of medical devices, each of the one or more bands 340 may be positioned a respective distance from a distal end 342 of the elongate member. The bands 340 may be visible, either fluoroscopically or endoscopically, and their visibility provides indications of where the bands 340 as well as objects or substances (such as those at treatment site within a patient) are relative to the distal end 342. For some example configurations, the bands 340 may be made of a metallic material and/or may be radiopaque bands made of a fluoroscopically visible material such as tantalum or platinum as examples In addition to the bands 340, a heat shrink tube 322 may be disposed over the outer surface 326 at the distal portion 310 such that the heat shrink tube 322 covers each of the bands 340. The heat shrink tube 322 may have an original diameter that decreases or shrinks in response to heat, similar to that shown and described with reference to FIGS. 2A and 2B. In addition, the heat shrink tube 322 may be made of any material that shrinks in response to heat, and may have a higher, a lower, or the same surface energy as the surface energy of the material making up the body 324. Further, the material of the heat shrink tube 322 may be translucent to a degree such that the bands 340 do not lose their visibility characteristics. With the addition of the heat shrink tube 322, the bands 340 may be more securely or fixedly coupled to the outer surface 326 than if the heat shrink tube 322 were not included.

Figure 4A:
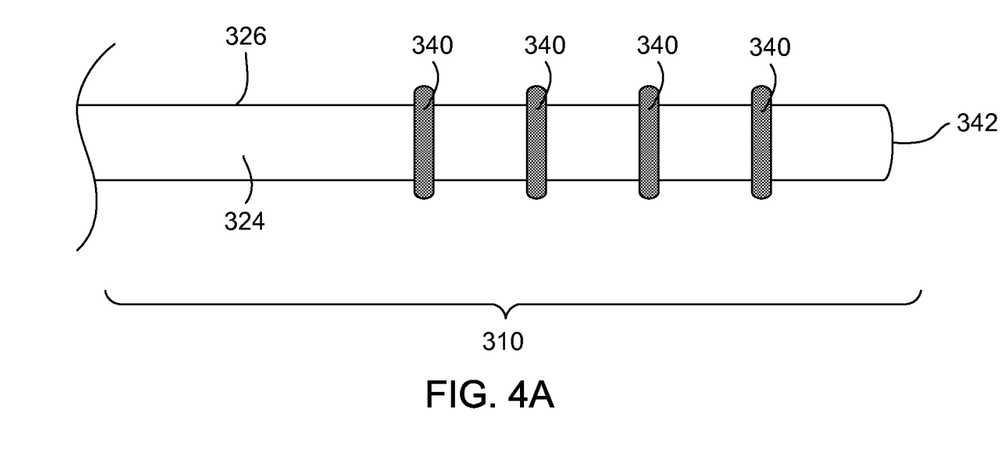
FIG. 4A shows a perspective side view of the distal portion of the elongate member of FIG. 3, where the bands are in an initial state.
Figure 4B:
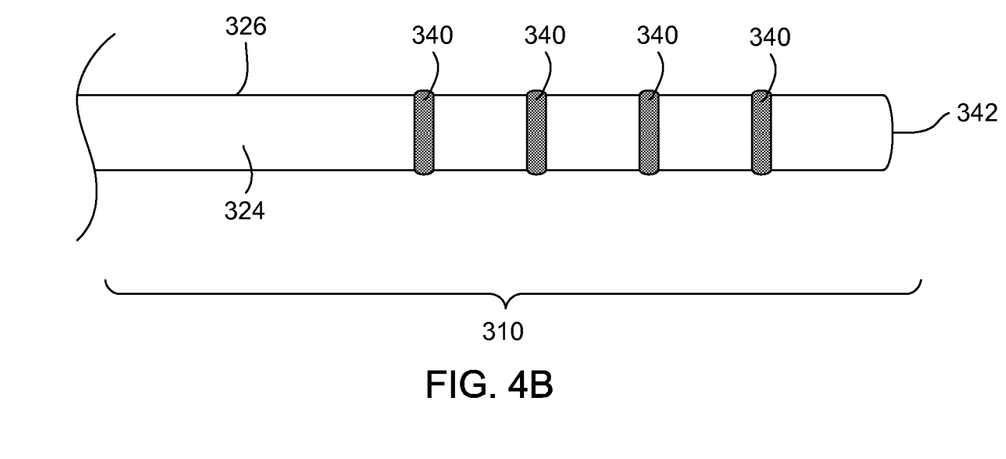
FIG. 4B shows a perspective side view of the distal portion of the elongate member of FIG. 3, where the bands are in a deformed state following an initial attachment procedure.
Figure 4C:
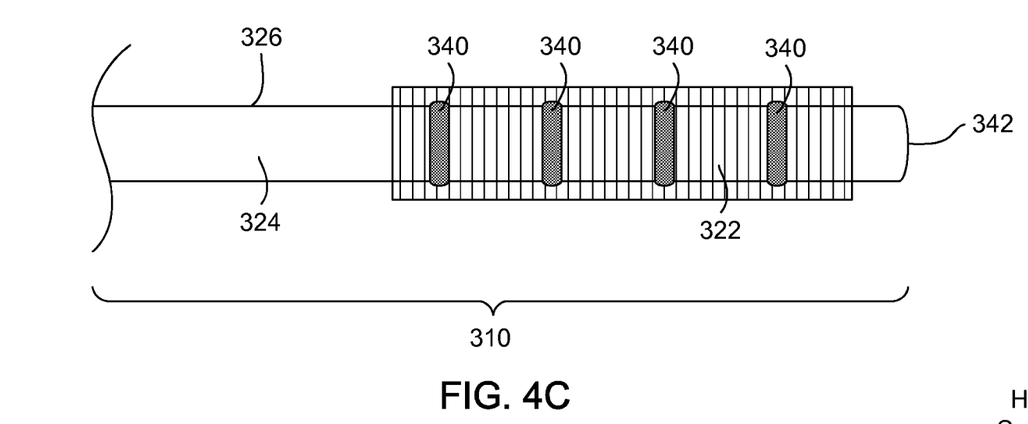
FIG. 4C shows a perspective side view of the distal portion of the elongate member of FIG. 3, where the bands are in a deformed state and a heat shrink tube in an initial state is disposed over the bands.
Figure 4D:
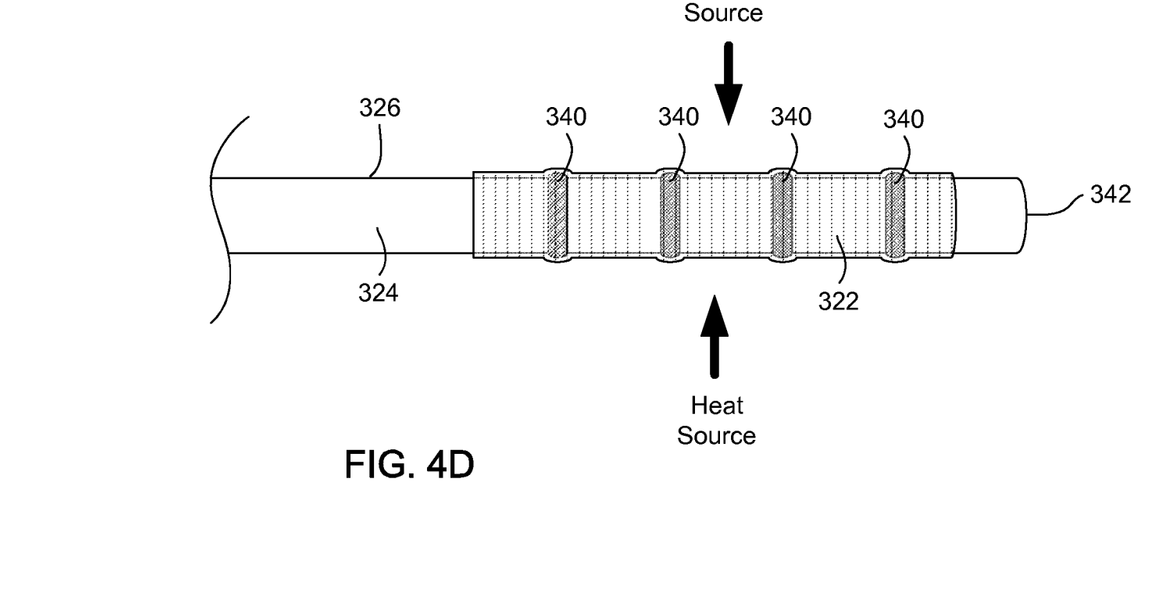
FIG. 4D shows a perspective side view of the distal portion of the elongate member of FIG. 3, where the heat shrink tube is in a shrunken state disposed over the bands.

To manufacture the elongate member 306 shown in FIG. 3, the bands 340 may first be longitudinally positioned over the distal portion 310 at the their respective positions relative to the distal end 342, as shown in FIG. 4A. After positioning the bands 340 in their respective positions, an initial attachment procedure, such as swaging or crimping, may be performed on the bands, which may reduce the diameter or otherwise deform the shape of the bands 340 to more securely affix the bands 340 to the outer surface 326, as shown in FIG. 4B. Following the initial attachment procedure, the heat shrink tube 322 with its original diameter may be disposed over the outer surface 326 at a longitudinal position such that it also covers the bands 340, as shown in FIG. 4C. After the heat shrink tube 322 is longitudinally positioned, heat may be applied to the heat shrink tube 322, causing the diameter of the heat shrink tube 322 to shrink and compress around bands 340, as shown in FIG. 4D. The shrinkage of the heat shrink tube 322 and compression over the bands 340 in response to the heat may more securely or fixedly couple the bands 340 to the outer surface 326.

For other example methods of manufacture, the initial attachment procedure may be performed after the heat shrink tube 322 is disposed over the bands 340 and before or after heat is applied to the heat shrink tube 322, or may be skipped altogether.

Figure 5:
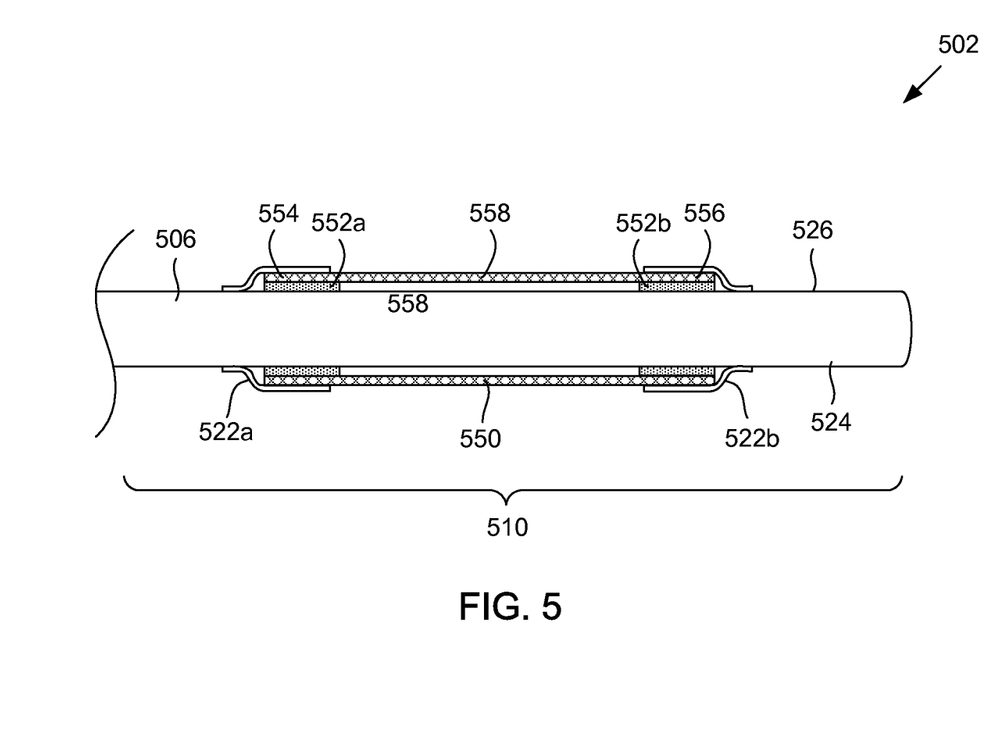
FIG. 5 shows a cross-sectional side view of a distal portion of an example balloon catheter.

FIG. 5 shows a cross-sectional side view of a distal portion 510 of an example balloon catheter 502 that includes an elongate member 506 having a body 524 and a balloon or other expandable structure 550 disposed over and fixedly coupled to an outer surface 526 of the body 524. The balloon 550 may be made of various materials, including latex, silicone, or polyurethane, although other materials may be possible. The body 524 may be made of a high surface energy material. An adhesive 552, such as cyanoacrylate glue, may be disposed on the outer surface 526. As shown in FIG. 5, the adhesive 552 may include two portions, such as rings, 552a, 552b longitudinally separated by a distance determined by the balloon 550 so that opposing ends 554, 556 of the balloon 550 are each affixed to a respective adhesive band 552a, 552b, and a middle section 558 of the balloon is detached from the adhesive 552 and the body 524. This configuration may allow the balloon 550 to expand and contract in order to perform a medical procedure.

The elongate member 506 may further include a pair of heat shrink tubes 522a, 522b each disposed over and covering a respective end 554, 556 of the balloon 550 and a respective one of the adhesive bands 552a, 552b. When heat is applied to the heat shrink tubes 552a, 552b, they may compress over and exert a radially inward force on the respective balloon ends 554, 556 and adhesive bands 552a, 552b. The exerted force may provide a more secure coupling of the adhesive 552 and the balloon 550 to the outer surface 526 of the body 524, compared to configurations where the heat shrink tubes 522a, 522b are not included. Additionally, the heat shrink tubes 522a, 522b may provide longitudinally smoother transitions between the outer surface 526 and the balloon ends 554, 556, which may provide an overall lower profile for the balloon catheter 502 and facilitate movement to and from the treatment site within the patient.

Figure 6:
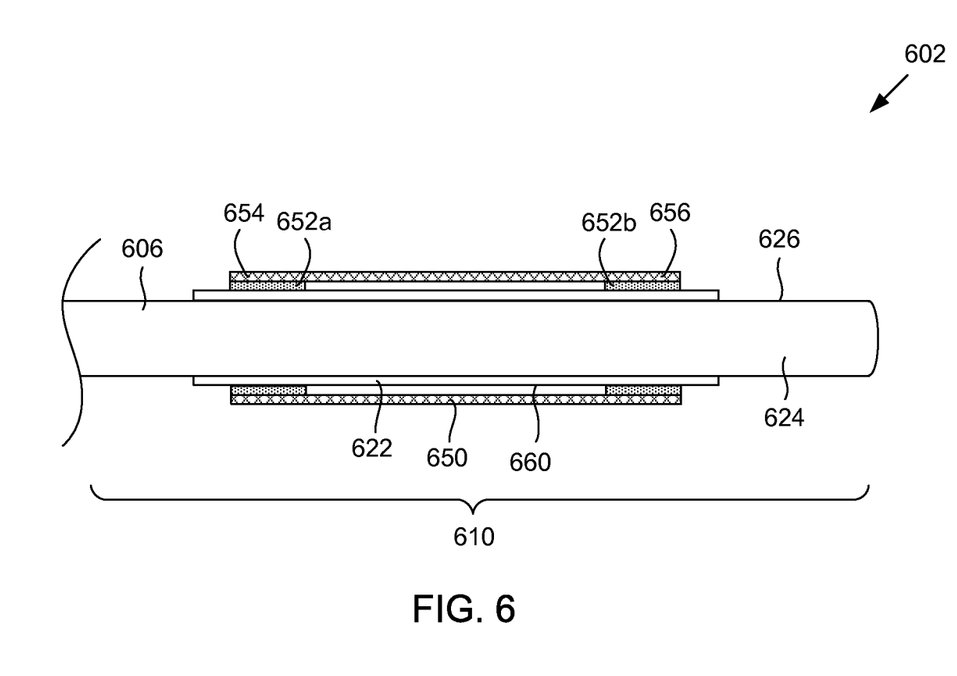
FIG. 6 shows a cross-sectional side view of a distal portion of another example balloon catheter.

FIG. 6 shows a cross-sectional side view of a distal portion 610 of another example balloon catheter 602 that includes an elongate member 606 having a body 624 and a balloon or other expandable structure 650 disposed over and fixedly coupled to an outer surface 626 of the body 624. Similar to the balloon catheter 502 shown in FIG. 5, an adhesive 652, including adhesive bands 652a, 652b, may be used to couple respective balloon ends 654, 656 to the outer surface 626. However, for the example catheter 602, the body 624, or at least the outer surface 626, may be made of a low surface energy material, and so the adhesive bands 652a, 652b may not sufficiently adhere to the outer surface 626. A heat shrink tube 622 made of a high surface energy material, or at least having a higher surface energy than that of the outer surface 626, may be disposed over and affixed to the outer surface 626 before the adhesive 652 is applied. The higher surface energy material of the heat shrink tube 622 may provide a greater strength of adhesion for the adhesive 652. After the heat shrink tube 622 is affixed to the outer surface 626, the adhesive 652 may be applied to the outer surface 660 of the heat shrink tube 622. In this way, the heat shrink tube 622 fixedly couples the adhesive 652 and the balloon catheter 660 to the outer surface 626 of the body 624, which is made of a low surface energy material. Although the heat shrink tube 622 is shown in FIG. 6 as a single structure, it may alternatively be configured as a pair of tubes, each for coupling a respective one of the adhesive bands 652a, 652b to the outer surface 626.

Application of a first cover to a surface of an object to enhance the coupling between the surface and a second cover as described in the present description is not limited to outer surfaces of elongate members, including those used for medical devices, but may be applicable to any object having a surface to which a cover or coating is to be applied but that coating or cover does not sufficiently adhere to the object's surface due to the surface's low surface energy. The first cover may increase or enhance the effective adhesive strength of the surface by having a greater surface energy than the surface energy of the object's surface. Additionally, the first cover may be any structure or made of any material capable of being fixedly coupled to the surface. The present description describes the first cover as being a heat shrink tube that exerts a radially inward force on the outer surface, which prevents longitudinal movement of the heat shrink tube relative to the body. In other example configurations, similar heat shrink structures other than tubes may be used, such as wraps or films, and the way in which the heat shrink structures are configured with respect to and/or are attached to the surface may depend on and/or correspond to the shape or other characteristics of the object.

In still other example configurations, the first cover may not be a heat shrink structure that does not shrink or otherwise respond to heat to be affixed to the surface. For these other example configurations, ways other than application of heat to the first cover may be used to affix the first cover to the surface of the object. For example, an adhesive may be applied to an inner surface of the first cover that contacts and/or faces the surface of the object and/or may be applied over outer edges of the first cover to affix the first cover to the surface. In addition or alternatively, metal bands may be positioned over outer edges of the first cover and crimped or otherwise deformed to secure the first cover to the surface of the object. In addition or alternatively, heat shrink structures may be positioned over outer edges of the first cover, and heat may be applied to those heat shrink structures. In response to the heat, those heat shrink structures may secure the first cover to the surface of the object. Various other examples for the first cover and/or ways to secure the first cover to the may be possible.

Further, the first cover may have other functions or provide other features in addition to fixedly coupling a second cover to a surface of an object. For example, additives may be included in the heat shrink resin that enhance manufacturing or production of visual indicators, such as by providing ultraviolet blocking, laser marking, and/or radiopaque visibility, as examples.

The foregoing description of various embodiments of the invention has been presented for purposes of illustration and description. It is not intended to be exhaustive or to limit the invention to the precise embodiments disclosed. Numerous modifications or variations are possible in light of the above teachings. The embodiments discussed were chosen and described to provide the best illustration of the principles of the invention and its practical application to thereby enable one of ordinary skill in the art to utilize the invention in various embodiments and with various modifications as are suited to the particular use contemplated. All such modifications and variations are within the scope of the invention as determined by the appended claims when interpreted in accordance with the breadth to which they are fairly, legally, and equitably entitled.

The invention claimed is:

1. An elongate member comprising:
   a body comprising an outer surface, wherein the outer surface comprises a first material having a first surface energy;
   a heat shrink structure disposed on the outer surface of the body, the heat shrink structure, in a heat shrunk state, fixedly attached to the body through exertion of a radially inward force on the outer surface of the body, wherein the heat shrink structure comprises a second material having a second surface energy that is greater than the first surface energy; and
   a conductive cover disposed on the heat shrink structure such that the heat shrink structure is disposed in between the outer surface of the body and the conductive cover, the conductive cover comprising one of a conductive ink or a conductive paste,
   wherein the heat shrink structure fixedly couples the one of the conductive ink or the conductive paste to the outer surface of the body.

2. The elongate member of claim 1, wherein the first material has a contact angle of less than 72 degrees.

3. The elongate member of claim 1, wherein the first material is Polytetrafluoroethylene.

4. The elongate member of claim 1, wherein the second material is nylon.

5. The elongate member of claim 1, wherein the heat shrink structure is transparent.

6. The elongate member of claim 1, further comprising a lumen longitudinally extending in the body.

7. The elongate member of claim 6, further comprising an elongate conductive member longitudinally extending in the lumen, wherein a cutting edge of the elongate conductive member distally extends outside the body from an opening to an anchor point.

8. The elongate member of claim 7, wherein the heat shrink structure is longitudinally disposed entirely between the opening and the anchor point.

9. The elongate member of claim 7, wherein the heat shrink structure longitudinally extends proximally past the opening.

10. The elongate member of claim 7, wherein the one of the conductive ink or the conductive paste is a return electrode for electrical current flowing through the elongate conductive member.

* * * * *